United States Patent [19]
Dansereau et al.

[11] Patent Number: 5,622,721
[45] Date of Patent: Apr. 22, 1997

[54] DOSAGE FORMS OF RISEDRONATE

[75] Inventors: Richard J. Dansereau, Sherburne; Russell Y. Mosher, Norwich; Douglas W. Axelrod, Norwich; William K. Sietsema, Norwich, all of N.Y.

[73] Assignee: The Procter & Gamble Company, Cincinnati, Ohio

[21] Appl. No.: 307,495

[22] Filed: Sep. 14, 1994

Related U.S. Application Data

[63] Continuation of Ser. No. 796,151, Nov. 22, 1991, abandoned.

[51] Int. Cl.$^6$ ................................. A61K 9/16; A61K 9/50
[52] U.S. Cl. .................. 424/490; 424/489; 424/463; 424/486; 424/482
[58] Field of Search ........................... 424/480, 490, 424/468, 482, 489, 488, 486

[56] References Cited

U.S. PATENT DOCUMENTS

| | | | |
|---|---|---|---|
| 4,716,041 | 12/1987 | Kjornaes | 424/468 |
| 4,786,505 | 11/1988 | Lovgren | 424/482 |
| 5,096,717 | 3/1992 | Wirth et al. | 424/490 |
| 5,431,920 | 7/1995 | Bechard et al. | 424/480 |

FOREIGN PATENT DOCUMENTS

| | | |
|---|---|---|
| 0186405 | 2/1986 | European Pat. Off. . |

Primary Examiner—Thurman K. Page
Assistant Examiner—William E. Benston, Jr.
Attorney, Agent, or Firm—K. F. Clark; M. P. McMahon; J. C. Rasser

[57] ABSTRACT

The present invention is directed to a novel enteric-coated oral dosage form of a risedronate active ingredient comprised of a safe and effective amount of a pharmaceutical composition which is comprised of a risedronate active ingredient and pharmaceutically-acceptable excipients. Said dosage forms prohibit the exposure of the risedronate active ingredient to the epithelial and mucosal tissues of the buccal cavity, pharynx, esophagus, and stomach and thereby protects said tissues from erosion, ulceration or other like irritation. Accordingly, the said dosage forms effect the delivery to the lower gastrointestinal tract of said human or other mammal of a safe and effective amount of the risedronate active ingredient, and substantially alleviate the esophagitis or esophageal irritation which occasionally accompanies the oral administration of risedronate active ingredients.

25 Claims, No Drawings

DOSAGE FORMS OF RISEDRONATE

This is a continuation of application Ser. No. 07/796,151, filed on Nov. 22, 1991 now abandoned.

TECHNICAL FIELD

The present invention relates to novel oral dosage forms of the diphosphonate compound, 3-pyridyl-1-hydroxyethylidene-1,1-bisphosphonic acid, hereinafter referred to as "risedronate". Said novel dosage forms are enteric-coated and delay the release of the risedronate until the lower gastrointestinal tract is reached, thereby protecting the epithelial and mucosal tissues of the mouth and the buccal cavity, the pharynx, the larynx, and the esophagus from erosion, ulceration, or other like irritation suffered by direct contact of these tissues with the risedronate active ingredient which may sometimes result from the oral administration of risedronate. This invention further relates to a method of treating or preventing diseases characterized by abnormal calcium and phosphate metabolism using the novel enteric coated dosage forms described herein.

BACKGROUND OF THE INVENTION

Polyphosphonic acids and their pharmaceutically-acceptable salts have been proposed for use in the treatment and prophylaxis of a number of pathological conditions which can affect humans or other mammals and involve calcium and phosphate metabolism. Such conditions may be divided into two broad categories:

1. Conditions which are characterized by anomalous mobilization of calcium and phosphate leading to general or specific bone loss or excessively high calcium and phosphate levels in the fluids of the body. Such conditions are sometimes referred to herein as patholological hard tissue demineralizations.

2. Conditions which cause or result from deposition of calcium and phosphate anomalously in the body. These conditions are sometimes referred to herein as pathological calcifications.

The first category includes osteoporosis, a condition in which bone hard tissue is lost disproportionately to the development of new hard tissue. Essential quantities of cancellous bone are lost, marrow and bone spaces become larger, resulting in reduced cancellar bone strength. Compact or bone also becomes less dense and fragile. Osteoporosis can be sub-classified as, senile, drug induced (e.g., adrenocorticoid, as can occur in steroid therapy), disease induced (e.g., arthritic and tumor), etc., however, the manifestations are similar. Another condition in the first category is Paget's disease (osteitis deformans). In this disease, dissolution of normal bone occurs which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastases are conditions also included in the first category.

The second category, involving-conditions manifested by anomalous calcium and phosphate deposition, includes myositis ossificans progressiva, calcinosis universalis, and such afflictions as arthritis, neuritis, bursitis, tendonitis and other inflammatory conditions which predispose involved tissue to deposition of calcium phosphates.

In particular diphosphonates, like ethane-1-hydroxy-1,1-diphosphonic acid (EHDP), propane-3-amino-1-hydroxy-1,1-diphosphonic acid (APD), and dichloromethane diphosphonic acid ($Cl_2MDP$) have been the subject of considerable research efforts in this area. Paget's disease and heterotopic ossification are currently successfully treated with EHDP. The diphosphonates tend to inhibit the resorption of bone tissue, which is beneficial to patients suffering from excessive bone loss. However, EHDP, APD and many other prior art diphosphonates have the propensity of inhibiting bone mineralization when administered at high dosage levels.

The compound risedronate is a more biologically potent diphosphonate compound which can be administered at low dosage levels; these lower dosage levels have resulted in a wider margin of safety and cause little or no mineralization inhibition. It is believed that the decrease in the inhibition of bone mineralization which is exhibited by the low dosage levels occurs because mineralization inhibition is predominately a mass related physiochemical effect, whereas resorption inhibition results from a biological interaction with the cells. In addition, low dosage levels are also desirable to avoid the gastrointestinal discomfort, like nausea, diarrhea, and abdominal pains, which are sometimes associated with the oral administration of disphosphonates.

Despite the low-dosage levels possible with risedronate, the oral administration of the compound sometimes results in patient complaints shortly after dosing; said complaints are usually characterized by the patients as heartburn, esophageal burning, pain and/or difficulty upon swallowing, and/or pain existing behind and/or mid-sternum. It is believed that these complaints originate from esophagitis or esophageal irritation caused by the erosion, ulceration, or other like irritation of the epithelial and mucosal tissues of the upper gastrointestinal tract, generally the mouth through the stomach, most generally the esophagus. It is hypothesized that said irritation results from the risedronate active ingredient coming in direct contact with those epithelial and mucosal tissues, resulting in the topical irritation thereof.

Accordingly, it became desirable to develop novel oral dosage forms of the risedronate compound which would prevent the release of risedronate compound in the area of said tissues. Said novel oral dosage forms are enteric coated and delay the beginning of the release of risedronate until some point in the small intestine or large intestine is reached and, thereby, provide protection to the tissues of the mouth, pharynx, and esophagus and stomach. Said novel enteric-coated oral dosage forms may be in the form of enteric-coated tablets or starch or gelatin capsules containing enteric-coated beads or particles.

SUMMARY OF THE INVENTION

The present invention is directed to a novel enteric-coated oral dosage form of a risedronate active ingredient comprised of a safe and effective amount of pharmaceutical composition which is comprised of a risedronate active ingredient and pharmaceutically-acceptable excipients. Said dosage forms prohibit the release of the risedronate active ingredient in the buccal cavity, pharynx, esophagus, and stomach thereby protects the epithelial and mucosal tissues thereof from erosion, ulceration or other like irritation.

Accordingly, the novel dosage forms described herein effect the delivery to the lower gastrointestinal tract of said human or other mammal of a safe and effective amount of the risedronate active ingredient, and substantially alleviate esophagitis or esophageal irritation which sometimes accompanies the oral administration of risedronate active ingredients.

The invention further comprises a method of treating diseases characterized by abnormal calcium and phosphate metabolism comprising administering to a human or other mammal afflicted with such a disease a novel oral dosage form as described herein.

DETAILED DESCRIPTION OF THE PRESENT INVENTION

The present invention is directed to a novel enteric-coated oral dosage form of a risedronate active ingredient comprised of a safe and effective amount of a pharmaceutical compostion which is comprised of a risedronate active ingredient and pharmaceutically-acceptable excipients. Said dosage forms prohibit the release of the risedronate active ingredient in the mouth, pharynx, and esophagus and thereby protects the epithelial and mucosal tissues thereof from erosion, ulceration or other like irritation. In addition, said dosage forms inhibit the release of the risedronate active ingredient to the stomach and anterior duodenum.

Accordingly, the said dosage forms effect the delivery to the lower gastrointestinal tract of said human or other mammal of a safe and effective amount of the risedronate active ingredient, and substantially alleviate esophagitis or esophageal irritation which occasionally accompanies the oral administration of risedronate active ingredients.

The invention further comprises a method of treating diseases characterized by abnormal calcium and phosphate metabolism comprising administering to a human or other mammal afflicted with such a disease a novel oral dosage form as described herein.

A. The Risedronate Active Ingredient

The term "risedronate", as used herein, denotes the diphosphonate compound 3-pyridyl-1-hydroxyethylidene-1,1-bisphosphonic acid and has the following structure:

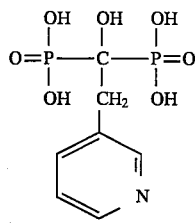

The compound risedronate is further described in the following publications, all hereby incorporated by reference herein: EPO Patent Application 0,186,405 of Benedict et al., assigned to The Procter & Gamble Co., published Jul. 2, 1986; and "An International Conference, Bisphosphonates: Current Status and Future Prospects, The Royal College of Physicians, London, England, May 21–22, 1990, organized by IBC Technical Services.

The term "risedronate active ingredient" includes risedronate, risedronate salts, and risedronate esters, or any mixture thereof. Any pharmaceutically-acceptable, non-toxic salt or ester of risedronate may be used as the risedronate active ingredient in the novel oral dosage forms of the present invention. The salts of risedronate may be acid addition salts, in particular the hydrochloride, but any pharmaceutically-acceptable, non-toxic organic or inorganic acid salt may be used. In addition, salts formed with the phosphonic acid group may be used, including, but not limited to, alkali metal salts (K, Na) and alkaline earth metal salts (Ca, Mg), the Ca- and Na- salts being preferred.

Particularly, other esters of risedronate which are suitable for use as the active ingredient in the invention disclosed herein are straight chain or branched chain $C_1$–$C_{18}$ alkyl esters, including, but not limited to, methyl, ethyl, propyl, isopropyl, butyl, isobutyl, amyl, hexyl, heptyl, octyl, nonyl, decyl, lauryl, myristyl, cetyl, and stearyl; straight chain or branched $C_2$–$C_{18}$ alkenyl esters, including, but not limited to, vinyl, alkyl, undecenyl, and linolenyl; $C_3$–$C_8$ cycloalkyl esters, including, but not limited to, cyclopropyl, cyclobutyl, cyclopentyl, cyclohexyl, cycloheptyl, and cyclooctyl; aryl esters, including, but not limited to, phenyl, toluyl, xylyl, and naphthyl; alicyclic esters, including, but not limited to, menthyl; and aralkyl esters, including, but not limited to, benzyl, and phenethyl.

Generally speaking, the proper selection of the risedronate active ingredient depends on the selected type of formulation, the disease pattern, especially the site and type of the disease, and the desired release of the active ingredient. In addition, the physical and chemical characteristics of the active ingredient must be taken into account when selecting suitable pharmaceutically-acceptable excipients for use in the novel dosage forms containing the risedronate active ingredient.

The effective oral dose of the risedronate active ingredient depends on the extent of the disease and for adults it usually amounts to from about 1 mg to about 40 mg daily, preferably from about 1 mg to about 30 mg daily. When the dose is to be administered continuously, the preferred dose is from 1–15 mg/day, preferably from 1–10 mg/day. When the dose is to be administered cyclically, the dose is preferably from 5–40 mg/day, preferably from 10–30 mg/day.

B. Site of Delivery of the Risedronate Active Ingredient

A human or other mammal suffering from diseases or disorders involving calcium and phosphate metabolism can be successfully treated by the delivery of the risedronate active ingredient to the lower gastrointestinal tract of said human or other mammal, preferably to the small intestine. The novel oral enteric-coated dosage forms described herein effect delivery to the lower gastrointestinal tract; at the same time prohibits the undesired release of risedronate in the mouth, pharynx and/or the esophagus, as well as inhibits the release of the risedronate active ingredient in the stomach, thereby prohibiting the erosion, ulceration or other like irritation of the epithelial or mucosal layers of these tissues. Although delivery to the small intestine alone is generally preferred, in some instances, however, it may be desired to deliver the risedronate active ingredient to the entire lower gastrointestinal tract, beginning with delivery to the small intestine and continuing with delivery to the large intestine; in other cases, delivery of the risedronate active ingredient to the large intestine only may be desired. When utilizing the novel enteric-coated oral dosage forms described herein, the pharmaceutically-acceptable excipients, coating methods, formulations, and/or thickness can be readily varied by one skilled in the art.

The term "gastrointestinal tract" as used herein relates to the alimentary canal, i.e., that musculo-membranous tube about thirty feet in length, extending from the mouth to the anus. The term "upper gastrointestinal tract" as used herein means the buccal cavity, the pharynx, the esophagus, and the stomach. The term "lower gastrointestinal tract" as used herein means the small intestine, and the large intestine.

The term "buccal cavity" means the mouth or oral cavity and is lined with a mucous membrane which is continuous with the integument of the lips and with the mucous lining of the pharynx.

The term "pharynx" relates to that part of the upper gastrointestinal tract which is placed behind the nose, mouth and larynx. It is a mucomembraneous tube about 4 inches in length and it is contiguous anteriorly with the mouth and posteriorly with the esophagus and is composed of a mucous coat, a fibrous coat, and a muscular coat.

The term "esophagus" as used herein is a muscular canal about nine inches long extending from the pharynx to the stomach. The esophagus has three coats: an internal mucous coat surrounding the lumen, a middle areolar coat, and an external muscular coat.

The term "stomach" as used herein means that part of the gastrointestinal tract between the esophagus and the small intestine.

The term "small intestine" as used herein means that part of the lower gastrointestinal tract consisting of the duodenum, the jejunum, and the ileum, i.e., that portion of the intestinal tract just distal to the duodenal sphincter of the fundus of the stomach and proximal to the large intestine.

The term "large intestine" as used herein includes that part of the lower gastrointestinal tract just distal to the small intestine, beginning with the cecum, including the ascending colon, the transverse colon, the descending colon, the sigmoid colon, and the rectum.

C. Novel Enteric-Coated Oral Dosage Forms for Delivery of the Risedronate Active Ingredient to the Lower Gastrointestinal Tract As stated hereinabove, the present invention is directed to novel enteric-coated oral dosage forms of the risedronate active ingredient to effect delivery to the lower gastrointestinal tract of a human or other mammal, preferably to the small intestine, of a pharmaceutical composition comprised of a safe and effective amount of a risedronate active ingredient and pharmaceutically-acceptable excipients.

The novel oral dosage form may be either delayed-release formulations or sustained-release formulations; said oral dosage forms prohibit the delivery of the risedronate active ingredient from the dosage form until it reaches the lower gastrointestinal tract of the individual. Accordingly, the tissues of the upper gastrointestinal tract, especially the epithelial and mucosal layers of the buccal cavity, the pharynx, esophagus and stomach from direct contact with the risedronate active ingredient. Said oral dosage form, therefore, substantially alleviates the esophagitis or esophageal irritation which occasionally occurs upon oral administration of pharmaceutical compositions containing a risedronate active ingredient. Accordingly, oral dosage forms suitable for use herein may be enteric-coated delayed-release formulations or enteric-coated sustained-release formulations. The dosage forms may be formulated as tablets or capsules, along with suitable pharmaceutical excipients which are well-known to those skilled in the art as described hereinbelow.

The term "pharmaceutical composition" means an oral dosage form comprised of a safe and effective amount of a risedronate active ingredient and pharmaceutically-acceptable excipients. The pharmaceutical compositions described herein are comprised of from 0.25% to 40.00%, preferably from 0.50% to 30.00% of a risedronate active ingredient and from 60.00% to 99.75%, preferably from 70.00% to about 99.50% of pharmaceutically-acceptable excipients.

The phrase "safe and effective amount", as used herein, means an amount of a compound or composition high enough to significantly positively modify the symptoms and/or condition to be treated, but low enough to avoid serious side effects (at a reasonable benefit/risk ratio), within the scope of sound medical judgment. The safe and effective amount of active ingredient for use in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular risedronate active ingredient selected for use. Pharmaceutically-acceptable excipients include, but are not limited to, polymers, resins, plasticizers, fillers, lubricants, solvents, co-solvents, buffer systems, surfactants, preservatives, sweetening agents, flavoring agents, pharmaceutical grade dyes or pigments, and viscosity agents. All or part of the pharmaceutically-acceptable excipients contained in the pharmaceuticaly compositions described herein is used to make the enteric-coating which is to be utilized in the novel oral dosage forms described herein.

The term "oral dosage form" as used herein means any pharmaceutical composition intended to be administered to the gastrointestinal tract of an individual via the mouth of said individual, and for purposes of the present invention, the delivered form can be in the form of a tablet, (preferably enteric-coated) containing granules or particles of risedronate active ingredient, or a capsule, (enteric-coated or non-coated), containing enteric-coated beads or enteric-coated granules of the risedronate active ingredient.

"Enteric-coated oral dosage form" as used herein relates to an oral dosage form containing a pharmaceutical composition as described herein which utilizes an enteric coating to effect the release of the risedronate active ingredient in the lower gastrointestinal tract. The enteric coated oral dosage from may be a compressed tablet (coated or uncoated) containing granules or particles of the risedronate active ingredient, which are themselves coated or uncoated. The enteric coated oral dosage form may be a gelatin capsule (coated or uncoated) containing beads or granules of risedronate active ingredient which are themselves coated or uncoated.

The term "enteric-coating" as used herein relates to a mixture of pharmaceutically-acceptable excipients which is applied to, combined with, mixed with or otherwise added to the risedronate active ingredients. The said coating may be applied to a compressed tablet, a gelatin capsule, and/or the beads, granules, or particles of risedronate active ingredient which are encapsulated into starch or gelatin capsules or compressed into tablets.

Accordingly, the said enteric coating is preferably applied to a compressed tablet which contains particles or granules of active ingredient; however, in the event the particles or granules are themselves enterically-coated before being compressed into a tablet, then the enteric coating of the compressed tablet itself is optional. The enteric coating is also applied to the beads or small particles of active ingredient which may be encapsulated into a starch or gelatin capsule. Said capsule may then be coated with said enteric coating, if desired. Because of their enteric coating, these novel dosage forms will prohibit the undesirable delivery of the risedronate active ingredient to the mucosal and epithelial tissues of the upper gastrointestinal tract, especially the mouth, pharynx and esophagus. Said coating also achieves the delivery of the active to the lower gastrointestinal tract at a point which can be manipulated by one skilled in the art by choosing the excipients which make up the coating, its type, and/or its thickness.

The term "delayed-release" as used herein refers to a delivery of a risedronate active ingredient which is effected by formulating the active ingredient in a pharmaceutical composition so that the release will be accomplished at some generally predictable location in the lower gastrointestinal tract more distal to that which would have been accomplished if there had been no alteration in the delivery of the active ingredient. The preferred method for effecting the delayed-release of the active ingredient involves coating (or otherwise encapsulating) said active ingredient with a substance which is not absorbed, or otherwise broken down, by the gastrointestinal fluids to release said active ingredient until a specific desired point in the intestinal tract is reached. The most preferred type of delayed-release formulation for use herein is achieved by coating the tablet, capsule, or particles, granules, or beads of active ingredient with a substance which is pH-dependent, i.e., broken down at a pH which is generally present in the small intestine, but not broken down at a pH which is generally present in the mouth, pharynx, esophagus or stomach. However, if it is desired to effect the topical delivery via the oral administration of a pharmaceutical composition containing the risedronate active ingredient to only the large intestine, or to the entire length of the intestinal tract beginning with the small intestine, then the selection of the coating material and/or the method of coating or otherwise combining the risedronate active ingredient with the selected coating material or other pharmaceutically-acceptable excipients may be varied or altered as is described herein or by any method known to one skilled in the art.

The term "sustained-release" as used herein means the type of release mechanism designed to effect the delivery of the active ingredient over an extended period of time, as contrasted to the delivery of a delayed-release type dose. The most preferred sustained-release type method for use herein involves the coating of granules of the risedronate active ingredient with a pH-independent coating, chosen from the group including, but not limited to ethylcellulose, hydroxypropylmethylcellulose, methylcellulose, hydroxymethylcellulose, hydroxyethylcellulose, and sodium carboxymethylcellulose. Various sustained-release dosage forms could readily be fashioned by one skilled in the art which could achieve the delivery of the risedronate active ingredient to both the small intestine and the large intestine, to only the small intestine, or to only the large intestine, depending upon the choice of the various coating materials, and/or coating thickness.

As stated hereinabove, the ultimate site of and/or the rate of topical delivery in the intestinal tract can be satisfactorily controlled by one skilled in the art, by manipulating any one or more of the following:

(a) the active ingredient proper;

(b) the type of the coating, and the concomitant desirable thickness and permeability (swelling properties) of said coating;

(c) the time-dependent conditions of the coating itself and/or within the coated tablet, particle, bead, or granule;

(d) the particle size of the granulated active ingredient; and (e) the pH-dependent conditions of the coating itself and/or within the coated tablet, particle, bead, or granule.

In particular, the solubility, acidity, and susceptibility to hydrolysis of the different risedronate active ingredients, such as acid addition salts, salts formed with the phosphonic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the coated tablets, particles, granules, or beads by adding a suitable buffer to the active ingredient in accordance with the desired release pattern.

Besides the above mentioned variations in order to obtain the desired release pattern, the excipients may also be varied, as long as they do not affect the activity of the particular risedronate active ingredient selected.

As stated hereinabove, pharmaceutically-acceptable excipients include, but are not limited to, polymers, resins, plasticizers, fillers, lubricants, solvents, cosolvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein.

Preferred co-solvents include, but are not limited to, ethanol, glycerin, propylene glycol, polyethylene glycol.

Preferred buffer systems include, but are not limited to, potassium acetate, boric, carbonic, phosphoric, succinic, malic, tartaric, citric, acetic, benzoic, lactic, glyceric, gluconic, glutaric and glutamic. Particularly preferred are phosphoric, tartaric, citric, and potassium acetate.

Preferred surfactants include, but are not limited to, polyoxyethylene sorbitan fatty acid esters, polyoxyethylene monoalkyl ethers, sucrose monoesters and lanolin esters and ethers.

Preferred preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben.

Preferred sweeteners include, but are not limited to, sucrose, glucose, saccharin, and aspartame. Particularly preferred are sucrose and saccharin.

Preferred viscosity agents include, but are not limited to, methylcellulose, sodium carboxymethylcellulose, hydroxypropylmethylcellulose, carbomer, povidone, acacia, guar gum, xanthan gum and tragacanth. Particularly preferred are methylcellulose, carbomer, xanthan gum, guar gum, povidone and sodium carboxymethylcellulose.

Preferred fillers include, but are not limited to, lactose, sucrose, maltodextrin, and microcrystalline cellulose.

Preferred plasticizers include, but are not limited to, polyethylene glycol, propylene glycol, dibutyl phthalate, and castor oil, acetylated monoglycerides, and triacetin.

Preferred polymers include, but are not limited to, ethylcellulose, hydroxypropylmethylcellulose phthalate, and cellulose acetate phthalate, polyvinyl acetate phthalate, and Eudragit L-30-D®, Eudragit L-100-55® and Eudragit S® 100, both manufactured by Rohm Pharma GmbH, Weiderstadt, West Germany, and Cotteric, manufactured by Colorcon, Inc., West Point, Pa.

Preferred lubricants include, but are not limited to, magnesium stearate, stearic acid, and talc.

Utilizing the novel oral dosage forms of the present invention, the risedronate active ingredient can be reliably delivered, specifically to the entire lower gastrointestinal tract, or any part thereof, preferably the small intestine, thereby prohibiting the undesired exposure of risedronate in the mucosal and epithelial tissues of the mouth, pharynx, and/or esophagus and inhibiting its release in the stomach. Said dosage forms render the risedronate active ingredient readily available for absorption from the lower gastrointestinal tract and, there is substantially no contact of the active ingredient upon the epithelial and mucosal tissues of the mouth, pharynx, esophagus, or stomach. Accordingly, the novel enteric-coated oral dosage forms of the present invention substantially alleviates the condition of esophagitis or esophageal irritation which occasionally results from the oral administration of a pharmaceutical composition comprising a risedronate active ingredient.

The most preferred oral dosage form which effects delivery to the small intestine is comprised of a risedronate active ingredient and utilizes a pH dependent enteric coating material made from a partly methyl esterified methacrylic acid polymer. Said solid oral dosage form can be in the form of a enteric coated compressed tablet made of granules or particles of active ingredient or a gelatin capsule which contain beads or small particles of active ingredient which have themselves been enterically coated.

While the coating method described immediately above is preferred, any enteric coating which is insoluble at a pH below 5.5 (i.e., that generally found in the mouth, pharynx, esophagus and stomach), but soluble at pH 5.5 or above (i.e., that present in the small intestine and the large intestine) can be used in the practice of the present invention. Accordingly, when it is desired to effect the topical delivery of the risedronate active ingredient to the small intestine, any enteric coating is suitable which is wholly- or partially-insoluble at a pH below 5.5 and soluble at pH 5.5 or above.

The partly methyl esterified methacrylic acid polymer which is preferred for use as the enteric coating must be applied to the compressed tablet, the gelatin capsule and/or the beads, particles or granules of active ingredient in a sufficient thickness so that the entire coating does not dissolve in gastrointestinal fluids at a pH below 5.5, but does dissolve at a pH of 5.5 or above. The dissolution or disintegration of the excipient coating generally does not occur until the entry of the coated dosage form into the small intestine. In particular, there is substantially no release of the risedronate ingredient upstream of the duodenum.

It is expected that any anionic polymer exhibiting the requisite pH-dependent solubility profile can be used as an enteric coating in the practice of the present invention to achieve delivery of the risedronate active ingredient to the lower gastrointestinal tract. The coating chosen must be compatible with the particular risedronate active ingredient selected. The preferred polymers for use in the present invention are anionic carboxylic polymers. It is particularly preferred that the polymers are acrylic polymers, most preferably partly methyl-esterified methacrylic acid polymers, in which the ratio of anionic free carboxyl groups to ester groups is about 1:1.

A particularly suitable methacrylic acid copolymer is Eudragit L®, particularly Eudragit L-30-D® and Eudragit 100-55®, manufactured by Rohm Pharma GmbH, Weiterstadt, West Germany. In Eudragit L-30-D®, the ratio of free carboxyl groups to ester groups is approximately 1:1. Further, said copolymer is known to be insoluble in gastrointestinal fluids having a pH below 5.5, generally 1.5–5.5, i.e., that generally present in the fluid of upper gastrointestinal tract, but readily soluble at pH above 5.5, i.e., that generally present in the fluid of the lower gastrointestinal tract.

Another methacrylic acid copolymer which is suitable for use in coating the oral dosage forms and/or the granules, particles or beads of active ingredient which can be employed in the method of treatment described herein, either alone or in combination with other coatings, is Eudragit S®, manufactured by Rohm Pharma GmbH, Weiterstadt, West Germany. Eudragit S® differs from Eudragit L-30-D® only insofar as the ratio of free carboxyl groups to ester groups is approximately 1:2. Eudragit S® is also, like Eudragit L-30-D®, insoluble at pH below 5.5, generally 1.5–5.5, such as that present in gastric juice, but, unlike Eudragit L-30-D®, is poorly soluble in gastrointestinal fluids having a pH of 5.5–7.0, such as that present in small intestinal juice. Said copolymer is soluble at pH 7.0 and above, i.e. that generally present in the colon.

Eudragit S® can be used alone as a coating which would provide delivery of the risedronate active ingredient beginning at the large intestine (more distal than the terminal ileum) via a delayed-release mechanism. In addition, Eudragit S®, being poorly soluble in intestinal juice below pH 7.0, could be used in combination with Eudragit L-30-D®, soluble in intestinal juice above pH 5.5, in order to effect a delayed-release composition which could be formulated to deliver the active ingredient at various segments of the intestinal tract; the more Eudragit L-30-D® used, the more proximal release and delivery begins and the more Eudragit S® used, the more distal release and delivery begins.

The coating can, and usually will, contain a plasticizer and possibly other coating excipients such as coloring agents, talc, and/or magnesium stearate, many of which are well known in the coating art. In particular, anionic carboxylic acrylic polymers usually will contain 10–25% by weight of a plasticizer, especially dibutyl phthalate, polyethylene glycol, triethyl citrate and triacetin. Conventional coating techniques such as spray or pan coating are employed to apply the coating. As previously mentioned, the coating thickness must be sufficient to ensure that the oral dosage form remains intact until the desired site of topical delivery in the lower intestinal tract is reached.

As stated hereinabove, the solid oral dosage form may be in the form of a coated compressed tablet which contains particles or granules of the risedronate active ingredient or of a gelatin capsule, coated or uncoated, which contains beads of the risedronate active ingredient, which themselves are enteric coated.

A. Enteric-Coated Tablets

One of the novel oral dosage forms of risedronate active ingredient which is preferred is enteric-coated compressed tablets. Tablets are made combining, mixing or otherwise adding the risedronate active ingredient to suitable pharmaceutical excipients including, but not limited to, sucrose, maltodextrin, lactose, microcrystalline cellulose, talc, magnesium stearate, crospovidone, and sodium starch glycolate. That mixture is then compressed into a tablet utilizing various tableting techniques available to those skilled in the art. The compressed tablet is then coated with an enteric-coating material which is made with suitable pharmaceutical excipients including, but not limited to, Eudragit L®, Eudragit L-30-D®, Eudragit 100-55®, Eudragit S®, hydroxypropylmethylcellulose phthalate, cellulose acetate phthalate, polyvinyl acetate phthalate cellulose acetate trimellatate, polyethylene glycol 400-8000, triacetin, dibutyl phthalate, acetylated monoglycerides, triethyl citrate talc, and iron oxide. The enteric-coating material is then applied to the compressed tablet utilizing numerous spraying techniques available to those skilled in the art.

The enteric-coating of the tablets is not soluble in the fluids of the mouth, the pharynx, the esophagus, or the stomach and thereby prohibits the release of risedronate until the lower gastrointestinal tract is reached, preferably the small intestine. Although it is not a preferred dosage form, one suitable dosage form which would effect delivery of the risedronate active ingredient to the lower gastrointestinal tract and thereby protect the mucosal tissues of the mouth, esophagus, and stomach would be an uncoated compressed tablet containing with enteric-coated beads, granules, or particles of the risedronate active ingredient.

For ease and cost-effectiveness of manufacture, however, the preferred novel dosage form described herein consists of enteric-coated compressed tablets which contain uncoated particles or granules of the risedronate active ingredient. In addition, some active ingredients are moisture sensitive and perform better if delivered in a tablet dosage form.

For the preferred coating method described herein utilizing methacrylate copolymers, when the desired site of delivery is the small intestine, it has been found that a coating thickness of between 20 and 100 microns usually is required. Preferably, the coating thickness is between 30 and 75 microns, and most preferably between 30 and 50 microns. For Examples of a method suitable for use in coating a compressed tablet containing the risedronate active ingredient which will effect the delivery of said active ingredient to the small intestine, see Examples I and II.

Another delayed-release type of compressed tablet suitable for achieving topical delivery of the risedronate active ingredient to the large intestine involves the use of a material, most preferably a resin, the dissolution of which is time-dependent, as opposed to the previously-mentioned methacrylic acid copolymer-type coatings which are pH-dependent. The delivery of said active ingredient to the small intestine is accomplished by embedding individual particles of said active ingredient in a slowly-disintegrating or slowly-dissolving resin which has a particular dissolution profile such that the active ingredient remains substantially protected by the material while the particles travel through the mouth, pharynx, esophagus and stomach of an individual and that the active ingredient is substantially completely exposed at the time the particles reach the small intestine. In particular, the preferred resin for use when employing this type of excipient material is a high-viscosity grade modified vinyl acetate resin such as Gelva C3-V30®, manufactured by The Monsanto Co., St. Louis, Mo. Other suitable resins are carboxylated polyvinyl acetates, polyvinyl/maleic anhydride copolymers, ethylcellulose, cellulose polymers, methacrylate acid/methyl methacrylate copolymers, waxes, and mixtures thereof, including mixtures with shellac.

While the preferred oral dosage form described herein is a coated delayed-release tablet containing a risedronate active ingredient, most preferably a release beginning in the small intestine, other methods used to insure the delivery of the risedronate active ingredient to the intestinal tract can certainly be utilized. For example, a suitable dosage form consists of enteric-coated granules or particles of risedronate in a sustained-release tablet and utilizes a polymer as the coating material; said polymer is preferably chosen from the group consisting of ethylcellulose, hydroxypropylmethylcellulose, hydroxymethylcellulose, methylcellulose, hydroxycellulose, and sodium carboxymethylcellulose, preferably ethylcellulose.

Another sustained-release oral dosage form suitable for use in the delivery of the risedronate active ingredient to the intestinal tract is a tablet characterized by a core comprising a risedronate active ingredient, preferably in the form of a weak base or a weak acid, upon which core there is provided a first, inner layer of a diffusion membrane comprised of ethylcellulose and/or copolymers of polyethyl acrylate, methyl methacrylate, trimethylammonium ethyl methacrylate chloride, or mixtures thereof. Further, on said inner layer there is provided a second layer of an excipient material, preferably of anionic polymers, fatty acids, or mixtures thereof, having a $pk_a$ of about 4.5 to about 7.0, preferably about 6.0 to about 6.5. When this outer layer has been removed by dissolution upon passage of the composition into the small intestine with the higher pH, a slow but controlled release of the risedronate active ingredient from the core by diffusion through the diffusion membrane occurs due to the difference in concentration on each side of said membrane.

B. Enteric Coated Beads or Granules

Another novel oral dosage form for the oral administration of the risedronate active ingredient consists of gelatin or starch capsules which contain enteric-coated beads or granules of the active ingredient. The gelatin or starch capsules may themselves then be coated, if desired. The use of capsules which contain enteric coated beads is generally not preferred from a standpoint of manufacturing cost and difficulty. However, some active ingredients which must be given in relatively higher doses are sometimes difficult to compress into tablets. In addition, particularly when the active ingredient may be irritating to mucosal tissues, it may be preferred to deliver the drug in gelatin or starch capsules containing smaller particles, beads or granules which are enterically coated versus enterically coated tablets. In addition, when ingested with food, tablets often sit in the stomach until the digestion of food causes the opening of the pyloric sphincter and pushes the tablet into the duodenum. When uncoated gelatin or starch capsules are used, the gelatin or starch will break down in the stomach, releasing the enteric coated beads. The beads can move through the pylorus independently of the presence of food, and there is decreased risk of large amounts of the active risedronate agent sitting for any period of time in direct contact with the epithelial and mucosal tissues. As used herein, "beads" refers to particles containing the active ingredient which are prepared by applying the risedronate active ingredient to inert substrate spheres, or beads, preferably utilizing a polymer film.

The substrate bead, accordingly, is used as an inert substrate to which the risedronate active ingredient is applied. The beads may be made from one, or a mixture of, a group selected from, but not limited to, sucrose, mannitol, lactose, dextrose, sorbitol, cellulose, and starch, most preferably sucrose and starch. The preferred size of the inert substrate beads is in the range of from 0.25 mm to 7.00 mm, preferably 2.00 mm to 4.00 mm. In addition, suitable inert substrate beads may be purchased as pre-prepared, for example, non-pareil PG beads, manufactured by Crompton and Knowles, Mahwah, N.J., or Edward Mendell Co., Patterson, N.J.

The risedronate active ingredient must be affixed to the inert substrate beads. The most preferred method of affixing the active ingredient to the substrate bead is the use of a polymer film. In addition, if an active ingredient is chosen that is deliquescent, the polymer film will serve to prevent the active from picking up moisture. If the active ingredient chosen is unstable in any way, the polymer film may provide some stability. The polymer film preferably comprises a mixture of hydroxypropylmethylcellulose, ethylcellulose, polyvinylpyrrolidone, hydroxypropylcellulose and/or ethylcellulose, preferably hydroxypropylmethylcellulose and ethylcellulose; and a suitable plasticizer. Plasticizers suitable for use in the film include, for example, but are not limited to, polyethylene glycol, propylene glycol, triacetin, acetylated monoglycerides, phthalate esters, caster oil, dibutyl sebacate, triethyl citrate, and selected mixtures thereof. The preferred amount of plasticizer is 5 to 40%, more preferably 20 to 40%, of the amount of the polymer film.

In addition to the risedronate active ingredient, the polymer film may contain optional fillers, pigments, and dyes as described hereinabove.

Preferably, the polymer or polymer mix can consist of any combination that offers protection against moisture pickup and/or oxygen transfer, and which is designed for immediate release of the active ingredient by intestinal juice. The amount of risedronate active ingredient to be applied to the inert substrate beads may vary depending upon the concentration desired in the finished product. However, the weight of the applied film on the substrate bead is between 5–50% weight gain, preferably between 5–25% weight gain, and most preferably 5–10% weight gain.

After the inert substrate beads are coated with the active ingredient, they must be enterically coated. Said enteric coating is applied utilizing various spray techniques known to one skilled in the art. Said coating is applied to the beads of active ingredient at a thickness of 20–100 microns, preferably 30–75 microns, most preferably 30–50 microns.

It may be desired to coat granules of the risedronate active ingredient instead of spraying inert substrate beads with the active ingredient. Granules, as are used herein, means particles of active ingredient in combination with suitable pharmaceutically-acceptable excipients as described hereinabove. Although is it preferable to encapsulate the enteric-coated granules, using starch or gelatin capsules, for administration as an oral dosage from, the granules may also be compressed into tablets.

Granules can be obtained by extrusion of a moist kneaded mass followed by spheronization and drying. Granules with a regular molding are preferred, for example, rod-shaped or cylindrical, particularly spherical. Spherical pellet-type granules are preferred, with a diameter between about 0.30 and 1.50 mm, preferably between about 0.50 and 1.25 mm.

Suitable pharmaceutically-acceptable ingredients for making the granules to be used in the novel dosage forms described herein include, but are not limited to, lactose, cellulose, mannitol, sucrose, and starch.

The prepared granules of active ingredient are then coated with an enteric coating material prepared from the pharmaceutically-acceptable excipients, utilizing various coating techniques known to those skilled in the art. Said coating is applied to said granules of active ingredient at a thickness of 20–100 microns, preferably 30–75 microns, most preferably 30–50 microns.

The following non-limiting examples serve to further illustrate the novel oral dosage forms of the present invention.

EXAMPLE I

Enteric-Coated Risedronate Tablets

Enteric-coated Risedronate tablets are made by preparing a coating composition and compressed tablets containing the risedronate active ingredient, and then applying said coating composition to said tablets.

An enteric coating composition is prepared in the form of a lacquer containing the following excipients, per tablet:

A. Enteric Coating Suspension

| Excipients | |
|---|---|
| Euragit L-30-D ® (manufactured by Rohm Pharma GmbH, Weiterstadt, West Germany) | 33.400 mg |
| Polyethylene glycol | 1.00 mg |
| Talc | 2.500 mg |
| Yellow Iron Oxide | 0.034 mg |
| Simethicone emulsion | 0.800 mg |
| Purified Water | 75.000 mg |

The enteric coating is prepared utilizing the following method:

The talc and yellow iron oxide is added to a portion of purified water and mixed until uniform. The polyethylene glycol 8000 and the simethicone emulsion are added with continuous mixing. The resulting pigment suspension is next passed through a screen or a suitable mill to break up agglomerates. The Eudragit L-30-D® is screened and then added to a suitable vessel and diluted with a portion of the purified water. The pigment suspension is then added to the diluted Eudragit suspension and mixed until uniform.

In a suitable coating pan, the risedronate sodium tablets prepared as described below are warmed to about 35°–40° C. The enteric coating suspension is sprayed onto the tablets at approximately 50 grams per minute. When the spray cycle is completed, the temperature is reduced and the tablets are removed and dried at 30°–40° C. for approximately 1 hour.

A coating of 4 mg/cm$^2$ dried lacquer substance (i.e., about 45 microns thick) is applied by spraying the above composition onto risedronate active ingredient tablets, prepared in part B. below.

B. Risedronate Sodium Compressed Tablets

The enteric coating suspension prepared in Part A. above is sprayed onto 30 mg risedronate round-shaped tablets, each weighing 250 mg and each containing:

| Active ingredient | |
|---|---|
| Risedronate | 30.00 mg* |
| Excipients | |
| Lactose | 156.00 mg |
| Microcrystalline Cellulose | 60.50 mg |
| Crospovidine | 7.40 mg |
| Magnesium Stearate | 1.10 mg |

*This quantity of risdronate sodium is dtermined by assay and then adjusted to provide the designed dosage level of risedronate sodium on an anhydrous basis.

Tablets having the composition set forth above are prepared as follows:

The tablets are prepared by mixing the risedronate active ingredient with the microcrystalline cellulose in a twin shell blender. The blend is passed through an oscillator equipped with a 60 mesh screen. The milled blend is then returned to the twin shell blender along with the lactose and crospovidone and mixed until uniform. The magnesium stearate is added and mixed until adequate lubrication is achieved. Tablets are then compressed on a rotary tablet press.

EXAMPLE II

Capsules Containing Enteric-Coated Beads

Capsules containing enteric-coated beads are prepared by preparing enteric-coated beads, and then encapsulating them using a gelatin capsule. The beads consist of inert sugar spheres that are coated with a polymeric film which contains risedronate sodium and are prepared utlizing the procedure in part A below. The beads are next enteric-coated utilizing the procedure described in part B below.

A. Risedronate Sodium-Coated Beads

| Component | Mg/Capsule |
| --- | --- |
| Risedronate Sodium | 30.0* |
| Sugar Spheres, 20–25 mesh | 115.6 |
| Hydroxypropylmethylcellulose | 12.0 |
| Polyethylene Glycol 3350 | 2.4 |
| Purified Water | 155.6 |

*This quantity of risedronate sodium is determined by assay and then adjusted to provide the designed dosage level of risedronate sodium on an anhydrous basis.

The Risedronate Coated Beads are prepared as follows:

The purified water is heated and the hydroxypropylmethylcellulose is slowly added. When the hydroxypropylmethylcellulose is dispersed, the polyethylene glycol is added and the solution is allowed to cool to 30° C. or less. The risedronate sodium is cooled, then passed through a mill, if needed, to break up agglomerates, and then mixed with the polymer solution until uniform.

In a suitable coating column, the sugar spheres are warmed to approximately 25° C. and then the risedronate coating suspension prepared above is sprayed on by applying a coating of 5 mg/cm² dried lacquer substance about 50 microns thick to the beads. When the spray cycle is completed, the air is turned off and the beads are cooled to room temperature.

B. Enteric-Coated Beads

| Component | Mg/Capsule |
| --- | --- |
| Risedronate Sodium Coated Beads (prepared in Part A above) | 160.0 |
| Eudragit L-30-D ® (wet basis) | 106.0 |
| Talc USP | 16.90 |
| Triethyl Citrate NF | 3.20 |
| Simethicone Emulsion USP | 2.10 |
| Yellow Ferric Oxide NF | 0.04 |
| Purfified Water | 225.00 |

The talc is added and the yellow ferric oxide is added to a portion of the purified water and mixed until uniform. The triethyl citrate and the simethicone emulsion is added with continued mixing. The resulting pigment suspension is then passed through a screen or a suitable mill to break up agglomerates. The Eudragit L30-D® is screened and then added to a suitable vessel and diluted with a portion of the purified water. The pigment suspension is then added to the diluted Eudragit suspension and mixing is continued.

A talc slurry is prepared by dispersing the talc in a portion of purified water and mixing until the talc is uniform.

In a suitable coating column the risedronate sodium coated beads are warmed to the appropriate temperature. The enteric coating suspension having the composition described in part B is sprayed on the beads. The talc slurry is sprayed onto the enteric coated beads. When the spray cycle is completed, the air is turned off. The coated beads are stored at 40°–50° C. for a minimum of 12 hours before encapsulating. The beads are encapsulated utilizing a hard shell gelatin capsule using an appropriate capsule filler.

EXAMPLE III

Enteric-Coated Risedronate Tablets

Enteric-coated risedronate tablets are prepared as described below, utilizing the method set forth in Example I.

A coating composition is prepared from a lacquer containing the following excipients, per tablet:

| | |
| --- | --- |
| Coateric ® (manufactured by Colorcon, Inc., West Point, PA | 24.0 mg |
| Triacetin | 3.0 mg |
| Titanium Dioxide | 3.0 mg |
| Purified Water | 167.0 mg |

A coating weight of 10.0 w/w % dried lacquer substance (about 75 microns thick) is applied by conventional pan coating to 10 mg risedronate tablets, so that oval-shaped tablets, each weighing 300 mg, result. The composition of each tablet is as follows:

| Active ingredient | |
| --- | --- |
| Risedronate Sodium | 10 mg |
| Excipients | |
| Sorbitol | 142 mg |
| Starch 1500 | 142 mg |
| Silicon Dioxide | 1 mg |
| Stearic acid | 15 mg |

EXAMPLE IV

Capsules Containing Enteric-Coated Particles

Capsules containing enteric-coated particles are made by preparing particles of the risedronate sodium active ingredient, and then encapsulating them into a gelatin capsule. The particles have the following composition:

| | Mg/Capsule |
| --- | --- |
| Active Ingredient | |
| Risedronate Sodium | 25 mg |
| Excipients | |
| Lactose | 50 mg |
| Microcrystalline Cellulose | 50 mg |

A mixture of risedronate sodium, lactose, and microcrystalline cellulose is moistened with water and kneaded, extruded, and spheronized. The dried particles are subsequently coated with enteric coating material prepared as described in Example III.

The Enteric-Coating has the following composition:

| Component | |
|---|---|
| Euragit L-30-D ® | 90.0 |
| Triethylcitrate | 21.0 |
| Antifoam AF | 2.0 |
| Talc | 7.0 |
| Water | 275.0 |

The particles having the composition as described hereinabove are coated in a laminator with a coating mixture having the above composition.

The enteric coating is prepared utilizing the procedure set forth in Example II. In a suitable coating column, the particles are warmed to about 25° C., and enteric coating solution is applied to the particles by spraying a coating of 5 mg/cm² dried lacquer substance about 50 microns thick to the particles. When the spray cycle is completed, the air is turned of and the particles are cooled to room temperature.

The lacquered particles are powdered with talc and encapsulated utilizing capsules (Capsule size 0), with a commercial capsule filling machine (Hafliger and Karg).

What is claimed is:

1. A novel oral dosage form of a risedronate active ingredient comprised of a safe and effective amount of a pharmaceutical composition comprising a risedronate active ingredient and pharmaceutically-acceptable excipients, wherein said oral dosage form is enteric coated to prohibit delivery of risedronate active ingredient to the buccal cavity, pharynx, esophagus and stomach of humans and other mammals to thereby prevent irritation in said buccal cavity, pharynx, esophagus and stomach.

2. A dosage form according to claim 1 wherein said pharmaceutical composition is comprised of from 0.25% to 40.00% of a risedronate active ingredient and from 60.00 to 99.75% of pharmaceutically-acceptable excipients.

3. A dosage form according to claim 2 wherein the enteric coating is a pH-dependent coating and said oral dosage form is a delayed-release pharmaceutical composition.

4. A dosage form according to claim 3 wherein said enteric coating is insoluble at pH below 5.5 but soluble at pH 5.5 or above.

5. A dosage form according to claim 3 wherein said enteric coating is insoluble in the gastrointestinal fluids of the buccal cavity, pharynx, esophagus, and stomach, but soluble in the gastrointestinal fluids of the small and large intestine.

6. A dosage form according to claim 3 wherein said coating is comprised of anionic carboxylic polymers.

7. A dosage form according to claim 6 wherein said anionic carboxylic polymer is a partly-methyl-esterified methacrylic acid polymer wherein the ratio of anionic free carboxyl groups to ester groups is about 1:1.

8. A dosage form according to claim 3 wherein said enteric coating is insoluble at a pH below 7.0 and soluble in pH 7.0 or above.

9. A dosage form according to claim 8 wherein said enteric coating is insoluble in the gastrointestinal fluids of the buccal cavity, pharynx, esophagus, stomach, and small intestine but soluble in the gastrointestinal fluids of the large intestine.

10. A dosage form according to claim 9 wherein said coating is comprised of anionic carboxylic polymers.

11. A dosage form according to claim 10 wherein said anionic carboxylic polymer is a partly-methyl-esterified methacrylic acid polymer wherein the ratio of anionic free carboxyl groups to ester groups is about 1:2.

12. A dosage form according to claim 2 wherein the enteric coating is a pH-independent coating and said oral dosage form is a sustained-release pharmaceutical composition.

13. A dosage form according to claim 12 wherein said enteric coating is a polymer selected from the group consisting of ethylcellulose, hydroxypropylmethylcellulose, and carboxymethylcellulose.

14. A dosage form according to claim 12 wherein said dosage form is a tablet characterized by a core comprising a risedronate active ingredient upon which core there is provided a first inner layer of a diffusion membrane selected from the group consisting of ethylcellulose, polyethyl acrylate, methyl methacrylate, trimethylammonium ethyl methacrylate chloride, or mixtures thereof, and on said inner layer there is provided an outer layer of excipient material having a pKa of 4.5 to 7.0.

15. A novel oral dosage form according to claim 1 wherein said dosage form is a compressed tablet comprising particles of the risedronate active ingredient and pharmaceutically-acceptable excipients.

16. An oral dosage according to claim 15 wherein said compressed tablet is enterically coated.

17. An oral dosage form according to claim 15 wherein said compressed tablet is comprised of particles of risedronate active ingredient which have been enterically coated.

18. An oral dosage form according to claim 17 wherein said compressed tablet is enterically coated.

19. A novel oral dosage form according to claim 1 wherein said dosage form is a capsule containing beads of the risedronate active ingredient which are themselves enterically coated.

20. A novel oral dosage form according to claim 1 wherein said dosage form is a capsule containing granules of the risedronate active ingredient which are themselves enterically coated.

21. A novel oral dosage form according to claim 20 wherein said capsule is itself enterically coated.

22. A novel oral dosage form according to claim 19 wherein said capsule is itself enterically coated.

23. A method of treating diseases characterized by abnormal calcium and phosphate metabolism, comprising administering to a human or other mammal in need of such treatment a safe and effective amount of a risedronate active ingredient delivered to said human or other mammal the novel oral dosage form of claim 1.

24. A novel oral dosage form according to claims 16, 17, 18, 19, 20, 21 or 22 wherein the enteric coating is comprised of a pH-dependent coating material.

25. An oral dosage form according to claim 24 wherein said coating material is insoluble at a pH below 5.5 and soluble at a pH 5.5 or above.

* * * * *